United States Patent
Fox

(10) Patent No.: US 9,510,956 B2
(45) Date of Patent: Dec. 6, 2016

(54) PROSTHETIC SYSTEM

(71) Applicant: Biomet Manufacturing, LLC, Warsaw, IN (US)

(72) Inventor: Duke A. Fox, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 315 days.

(21) Appl. No.: 14/196,537

(22) Filed: Mar. 4, 2014

(65) Prior Publication Data
US 2014/0188235 A1    Jul. 3, 2014

Related U.S. Application Data

(60) Provisional application No. 61/791,223, filed on Mar. 15, 2013.

(51) Int. Cl.
A61F 2/46    (2006.01)
A61F 2/38    (2006.01)
A61F 2/30    (2006.01)

(52) U.S. Cl.
CPC ............. *A61F 2/461* (2013.01); *A61F 2/389* (2013.01); *A61F 2/3859* (2013.01); *A61F 2/4684* (2013.01); *A61F 2/3868* (2013.01); *A61F 2/4637* (2013.01); *A61F 2002/30405* (2013.01); *A61F 2002/30878* (2013.01); *A61F 2002/30884* (2013.01); *A61F 2002/3895* (2013.01)

(58) Field of Classification Search
CPC ...... A61F 2/4603; A61F 2/461; A61F 2/4611; A61F 2002/4622; A61F 2002/4623; A61F 2002/4624; A61F 2002/4625; A61F 2002/4627; A61F 2002/4628; A61F 2/389; B23B 5/082; B23B 5/101; B23B 5/125

USPC .................... 606/99; 269/143, 249
See application file for complete search history.

(56) References Cited

U.S. PATENT DOCUMENTS

| | | | | |
|---|---|---|---|---|
| 1,349,564 A | * | 8/1920 | Evits ....................... | B25B 13/16 81/164 |
| 1,387,996 A | * | 8/1921 | Menger ................... | B25B 5/101 269/249 |
| 1,405,140 A | * | 1/1922 | Lundberg ................ | B25B 13/16 81/155 |
| 1,412,961 A | * | 4/1922 | Periolat ................... | B25B 5/101 248/231.71 |

(Continued)

OTHER PUBLICATIONS

Oxford® Partial Knee Microplasty® Instrumentation Surgical Technique, Biomet Orthopedics, 2012, Form No. BMET0186.0.

(Continued)

*Primary Examiner* — Christian Sevilla
*Assistant Examiner* — Eric S Gibson
(74) *Attorney, Agent, or Firm* — Schwegman Lundberg & Woessner, P.A.

(57) ABSTRACT

An instrument for engaging a bearing configured to facilitate articulation of a femoral component and a tibial component. The instrument includes a first bearing engaging portion configured to engage a first end of the bearing, and a second bearing engaging portion configured to engage a second end of the bearing that is opposite to the first end. A coupling member of the instrument interconnects the first and the second bearing engaging portions. The coupling member is operable to move the second bearing engaging portion relative to the first bearing engaging portion to secure the bearing therebetween.

20 Claims, 6 Drawing Sheets

(56) References Cited

U.S. PATENT DOCUMENTS

| | | | | |
|---|---|---|---|---|
| 1,446,904 | A * | 2/1923 | Jones | B25B 9/00 279/59 |
| 1,533,688 | A * | 4/1925 | Bergh | B25B 5/08 269/221 |
| 1,587,820 | A * | 6/1926 | Carter | B25B 5/101 269/140 |
| 2,167,897 | A * | 8/1939 | Kulp | B25B 27/24 29/214 |
| 2,610,662 | A * | 9/1952 | Ratcliff | B25B 5/125 269/223 |
| 2,737,215 | A * | 3/1956 | Larson | B25B 5/101 269/249 |
| 2,863,477 | A * | 12/1958 | Sagerty | B25B 5/082 269/197 |
| 3,035,467 | A * | 5/1962 | Pirtle | B25B 13/16 81/164 |
| 3,046,821 | A * | 7/1962 | Legris | B25B 13/16 81/164 |
| 3,357,698 | A * | 12/1967 | Flynn | B25B 5/101 269/221 |
| 3,403,901 | A * | 10/1968 | Servadio | B25B 5/101 269/243 |
| 3,425,098 | A * | 2/1969 | Bredvik | B25B 5/12 220/324 |
| 4,901,963 | A * | 2/1990 | Yoder | B25B 5/103 24/489 |
| 5,018,711 | A * | 5/1991 | Johnson | B25B 5/067 269/249 |
| 5,090,670 | A * | 2/1992 | Yang | B25B 5/003 269/249 |
| 5,138,917 | A * | 8/1992 | Kirschner | B25B 9/00 81/164 |
| 5,312,097 | A * | 5/1994 | Womack | B25B 5/003 269/139 |
| 5,586,378 | A * | 12/1996 | Smith | B25B 27/023 269/249 |
| 5,713,117 | A * | 2/1998 | Bliss | B25B 27/023 29/257 |
| 5,732,992 | A * | 3/1998 | Mauldin | A61F 2/461 269/134 |
| 6,085,399 | A * | 7/2000 | Fileccia | B25B 27/023 29/239 |
| 6,123,326 | A * | 9/2000 | Kleinbongartz | B25B 5/068 269/143 |
| D450,991 | S * | 11/2001 | Nardozza | D8/73 |
| 6,319,257 | B1 * | 11/2001 | Carignan | A61F 2/4601 606/205 |
| 6,431,534 | B1 * | 8/2002 | Orosz | B25B 5/101 269/249 |
| 6,722,643 | B1 * | 4/2004 | Kurtz | B25B 5/10 269/249 |
| 7,040,199 | B2 * | 5/2006 | Gregory | B25B 13/5058 81/159 |
| 7,055,787 | B2 * | 6/2006 | Cross | B25B 5/003 248/226.11 |
| 7,261,593 | B1 * | 8/2007 | Deacon | B25B 5/003 439/574 |
| 7,588,223 | B2 * | 9/2009 | Wolvin | F16B 2/065 248/229.15 |
| 8,439,339 | B2 * | 5/2013 | Roesch | B25B 5/102 269/170 |
| 2001/0021876 | A1 * | 9/2001 | Terrill-Grisoni | A61F 2/3804 623/20.11 |
| 2004/0054373 | A1 * | 3/2004 | Serra | A61F 2/4637 606/102 |
| 2004/0217531 | A1 * | 11/2004 | Yates | B25B 1/125 269/184 |
| 2005/0209597 | A1 * | 9/2005 | Long | A61F 2/4607 606/86 R |
| 2006/0025864 | A1 * | 2/2006 | Lamprich | A61F 2/442 623/17.16 |
| 2006/0043662 | A1 * | 3/2006 | Blake, III | B25B 5/163 269/249 |
| 2006/0260442 | A1 * | 11/2006 | Simon | B25B 13/04 81/164 |
| 2007/0088362 | A1 * | 4/2007 | Bonutti | A61B 17/0218 606/99 |
| 2007/0245861 | A1 * | 10/2007 | Shields | B25B 13/5058 81/180.1 |
| 2008/0109004 | A1 * | 5/2008 | Da Rold | A61B 17/025 606/99 |
| 2008/0127794 | A1 * | 6/2008 | Jaksha | B25B 5/101 83/409 |
| 2009/0036909 | A1 * | 2/2009 | Perry | A61F 2/461 606/157 |
| 2009/0234364 | A1 * | 9/2009 | Crook | A61F 2/4465 606/99 |
| 2009/0234452 | A1 * | 9/2009 | Steiner | A61B 17/1764 623/14.12 |
| 2009/0240254 | A1 * | 9/2009 | Arnhold | A61F 2/461 606/99 |
| 2009/0326543 | A1 * | 12/2009 | Fabian, Jr. | A61F 2/4611 606/99 |
| 2010/0244348 | A1 * | 9/2010 | Castor | B25B 5/067 269/165 |
| 2011/0125202 | A1 * | 5/2011 | Ries | A61F 2/461 606/86 R |
| 2012/0025437 | A1 * | 2/2012 | Allred, III | B25B 5/101 269/249 |
| 2012/0277810 | A1 * | 11/2012 | Siccardi | A61F 2/4465 606/86 A |
| 2013/0026692 | A1 * | 1/2013 | Prins | B25B 5/101 269/249 |
| 2014/0114417 | A1 * | 4/2014 | Theofilos | A61F 2/4455 623/17.16 |
| 2014/0188235 | A1 * | 7/2014 | Fox | A61F 2/461 623/20.29 |
| 2014/0296929 | A1 * | 10/2014 | Stacey | A61F 2/461 606/86 R |
| 2014/0343559 | A1 * | 11/2014 | Flickinger | A61B 17/025 606/90 |
| 2015/0051606 | A1 * | 2/2015 | Khosla | A61F 2/461 606/99 |

OTHER PUBLICATIONS

Oxford® Partial Knee Twin Peg Femoral Component Phase III Instrumentation, Surgical Technique Addendum, Oxford® Partial Knee Surgical Technique (BOI0005.2), Biomet Orthopedics, 2011, Form No. BOI0472.0.

Oxford® Partial Knee, Biomet Orthopedics, 2011, Form No. BOI0233.2.

The Oxford® Partial Knee Surgical Technique, Biomet Orhopedics, 2009, 2010, Form No. BOI0005.2.

* cited by examiner

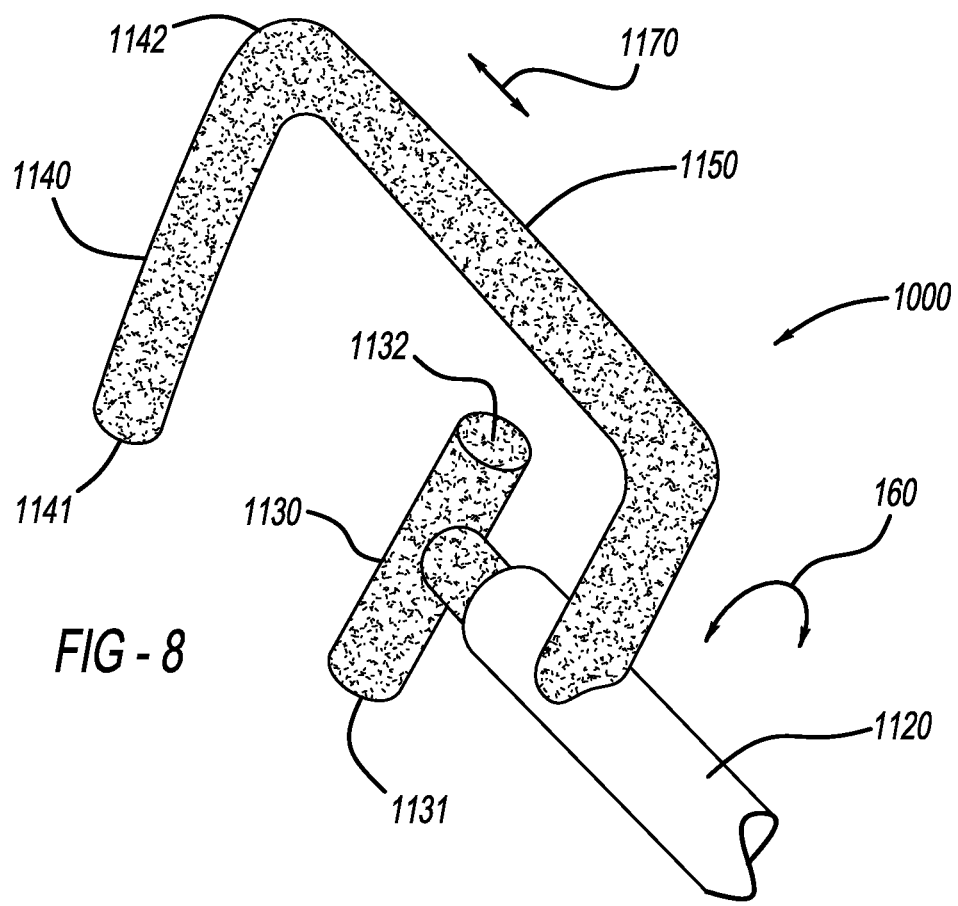
FIG - 8
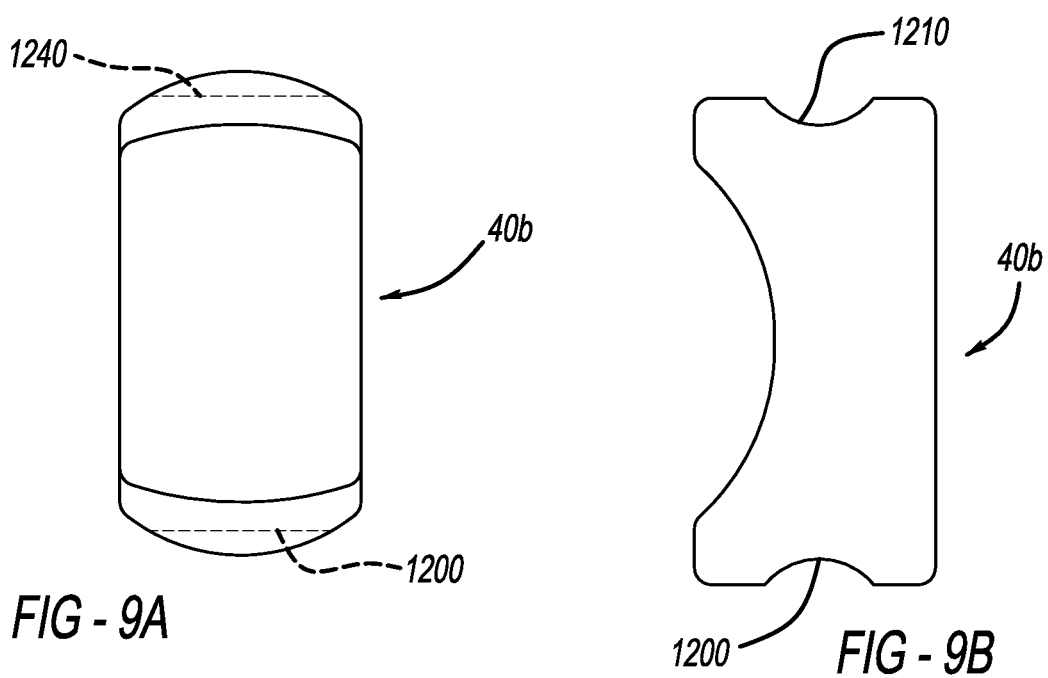
FIG - 9A
FIG - 9B

PROSTHETIC SYSTEM

CROSS-REFERENCE TO RELATED APPLICATION

This application claims the benefit of U.S. Provisional Application No. 61/791,223 filed on Mar. 15, 2013, the entire disclosure of which is incorporated herein by reference.

FIELD

The subject disclosure relates to a prosthetic system, and particularly to a knee prosthetic system.

BACKGROUND

This section provides background information related to the present disclosure, which is not necessarily prior art.

Various portions of an anatomy perform functions in a natural and, generally original, configuration. For example, bones can articulate relative to one another at joints. For example, at a knee joint a femur can articulate relative to a tibia in a generally natural state. The articulation between the femur and the tibia generally includes a medial condyle and a lateral condyle, and an inter-condylar region.

In the natural state, the articulation of the femur relative to the tibia can be pain-free and smooth due to various soft tissues between the two bones. Due to disease, injury, and other factors, the articulation between the femur and the tibia may become painful due to damage. The damage or painful region between the femur and the tibia may include all of the articulation regions or may only include damage to one of the condyles, such as the medial or the lateral condyle.

SUMMARY

This section provides a general summary of the disclosure, and is not a comprehensive disclosure of its full scope or all of its features.

The present teachings provide for an instrument for engaging a bearing configured to facilitate articulation of a femoral component and a tibial component. The instrument includes a first bearing engaging portion configured to engage a first end of the bearing, and a second bearing engaging portion configured to engage a second end of the bearing that is opposite to the first end. A coupling member interconnects the first and the second bearing engaging portions. The coupling member is operable to move the second bearing engaging portion relative to the first bearing engaging portion to secure the bearing therebetween.

The present teachings further provide for an instrument for engaging a bearing configured to facilitate articulation of a femoral component and a tibial component. The instrument includes a first bearing engaging portion configured to engage a first end of the bearing, and a second bearing engaging portion configured to engage a second end of the bearing that is opposite to the first end. A coupling member of the instrument includes an extension arm interconnecting the first and the second bearing engaging portions. The coupling member defines a throughbore from which the first bearing engaging portion extends. The extension arm extends parallel to and spaced apart from a longitudinal axis extending through an axial center of the throughbore. Rotation of the coupling member moves the coupling member along the longitudinal axis to move the second bearing engaging portion relative to the first bearing engaging portion.

The present teachings also provide for a method for positioning a bearing between a femoral component and a tibial component with a positioning instrument. The method includes the following: arranging a first bearing engaging portion of the instrument at a first end of the bearing; arranging a second bearing engaging portion of the instrument at a second end of the bearing that is opposite to the first end of the bearing; securing the instrument to the bearing by rotating in a first direction a coupling member of the instrument interconnecting the first and the second bearing engaging portions to move the second bearing engaging portion towards the first bearing engaging portion; positioning the bearing between the femoral component and the tibial component using the instrument; and rotating the coupling member in a second direction opposite to the first direction to move the first and the second bearing engaging portions apart and to decouple the instrument from the bearing.

According to various embodiments, a tool or instrument can be provided to insert a trial-bearing member and/or a prosthetic bearing member between a tibial and a femoral component. The tool can engage the bearing member to firmly hold the bearing member for insertion between the tibial and femoral member. Trialing can occur between the tibial and femoral member either while the tool engages the trial bearing or after the tool has been disengaged form the trial bearing. Additionally, the tool or instrument can position a prosthetic bearing member between the tibial and the femoral component and disengage the prosthetic bearing member for implantation of the prosthetic bearing.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

FIG. 8 is a perspective view of another bearing manipulation instrument according to various embodiments FIG. 9A and FIG. 9B illustrate another bearing according to the present teachings;

Corresponding reference numerals indicate corresponding parts throughout the several views of the drawings.

DETAILED DESCRIPTION

Example embodiments will now be described more fully with reference to the accompanying drawings.

Figure 1:
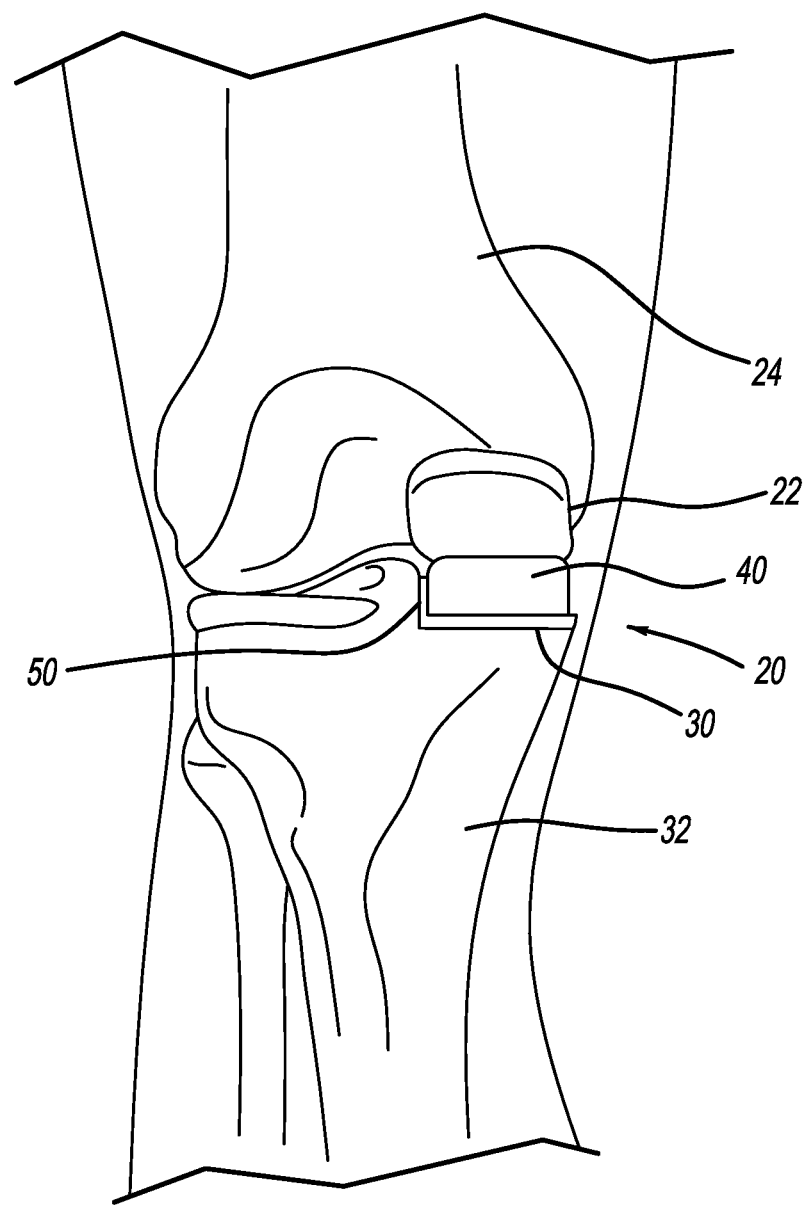
FIG. 1 is an environmental view of a femur, tibia, and prosthesis between the femur and tibia.

With reference to FIG. 1, a prosthetic system or prosthesis 20 is illustrated. The prosthetic system 20 can include a femoral component 22 that is interconnected with a femur 24 of a patient. The prosthetic system 20 can further include a tibial component 30 that is interconnected with a tibia 32. As illustrated in FIG. 1, the prosthetic system 20 is a uni-condylar prosthesis that is positioned on a medial portion of a leg of the patient. It is understood, however, that the prosthesis 20 can be positioned in a lateral condylar surface as well. Moreover, the prosthesis 20 can be positioned on both the medial and the lateral condyles of a single leg. Moreover the prosthesis 20 can be positioned on a left or a right leg.

Nevertheless, the prosthetic system 20 can further include a bearing member or component 40 that is positioned between the femoral component 22 and the tibial component 30. The bearing member 40 can articulate relative to the tibial component 30 and/or relative to the femoral component 22. As is understood in the art, the tibia 32 can bend and articulate relative to the femur 24 and the bearing member 40 contacts and allows smooth movement of the femoral component 22 relative to the tibial component 30. The bearing component 40, however, need not be fixed to the tibial component 30 and/or the femoral component 22.

As is further understood, although not specifically illustrated in FIG. 1, soft tissues can surround the knee near and within the condylar regions. For example, medial and lateral ligaments can extend exterior to the femur 24 and the tibia 32. The ligaments can interconnect and tightly surround the condylar region and the prosthesis 20. Moreover, as illustrated in FIG. 1 and in FIGS. 4 and 5, the tibia and/or the femur may be resected and/or otherwise prepared to receive the respective components. As illustrated in FIG. 1, a tibial wall 50 may be formed due to resection of the tibia 32. The tibial wall 50 can assist in maintaining the tibial component 30 in a selected position during placement and use of the prosthetic system 20. Accordingly, for example, during placement of a uni-condylar or partial knee prosthesis system, a working area may be substantially small. Moreover, an incision for inserting the uni-condylar prosthetic system 20 may also be substantially small. Various uni-condylar or partial knee prosthetic systems can include the Oxford® Partial Knee System as sold by Biomet, Inc.

Figure 2:
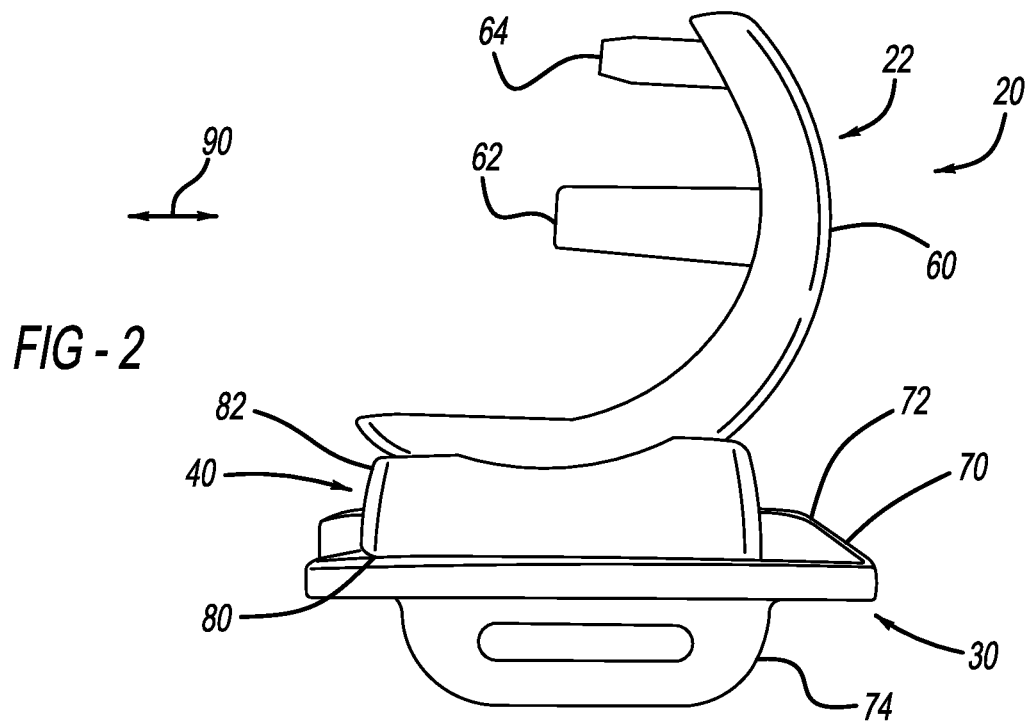
FIG. 2 is a side view of the prosthesis of FIG. 1.
Figure 3:
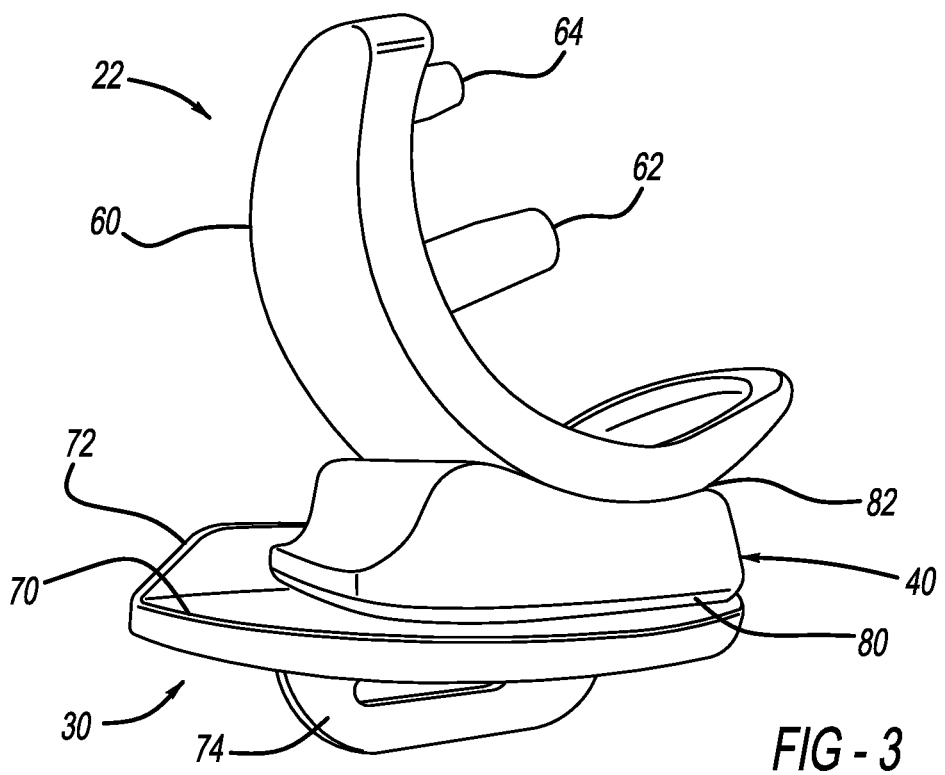
FIG. 3 is a perspective view of the prosthesis of FIG. 1.

As illustrated in FIGS. 2 and 3, the prosthetic system 20 can include the femoral component 22 that has a substantially smooth and polished exterior articulating surface 60. Additionally, post and/or fixation members can contact or be inserted into the femur. The post members can include a first post 62 and a second post 64. The femur 24 can be prepared by resecting selected portions of the femur and/or drilling bores to receive the posts 62 and/or 64.

The tibial component 30 can include a substantially polished and/or smooth upper surface 70, which can be an articulation surface, and a sidewall 72 that can also be substantially polished and/or smooth. A tibial fixation member 74 can extend from a surface opposite to the upper surface 70. Again, the tibia 32 can be prepared to receive the tibial component 30 by resecting the tibial component, such as forming the tibial wall 50, and/or forming a slot or groove the receive the tibial fixation member 74.

Positioned between the femoral component 22 and the tibial component 30 can be the bearing member 40. The bearing member 40 can include a tibial bearing side 80 and a femoral bearing side 82. Each of the respective bearing sides can include contoured surfaces to engage the respective components, such as a substantially flat surface to engage the upper tibial surface 70 and a concave surface to engage and articulate with the articulating surface 60 of the femoral component 22. Further, as discussed above, the bearing member 40 need not be fixed relative to either the femoral component 22 and/or the tibial component 30. Accordingly, the bearing member 40 can articulate anteriorly and posteriorly generally in the direction of arrow 90 due to movement of the femur 24 relative to the tibia 32 which causes movement of the femoral component 22 relative to the tibial component 30.

Figure 4:
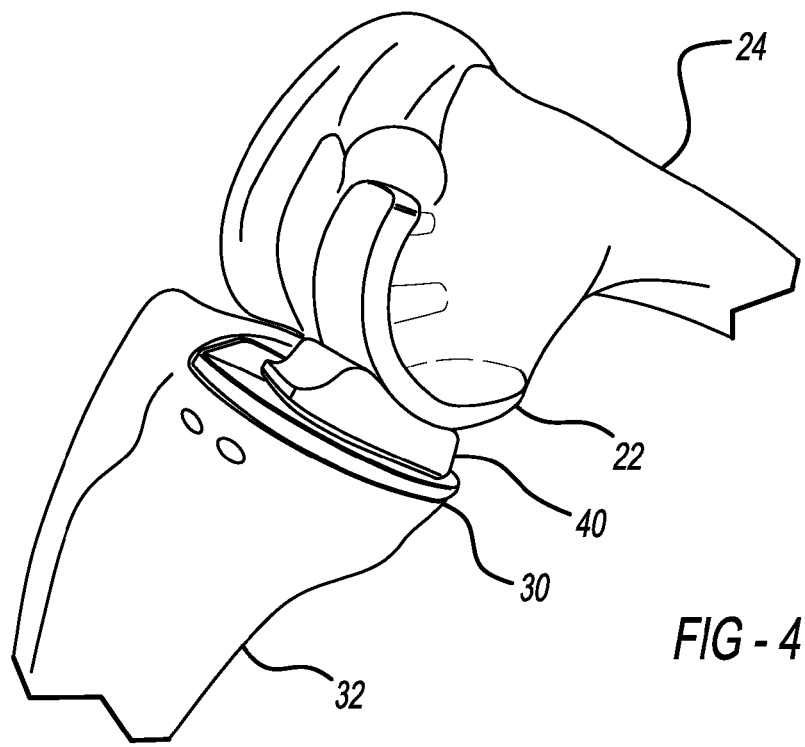
FIG. 4 is an environmental view of a femur, tibia, and prosthesis between the femur and tibia in flexion.
Figure 5:
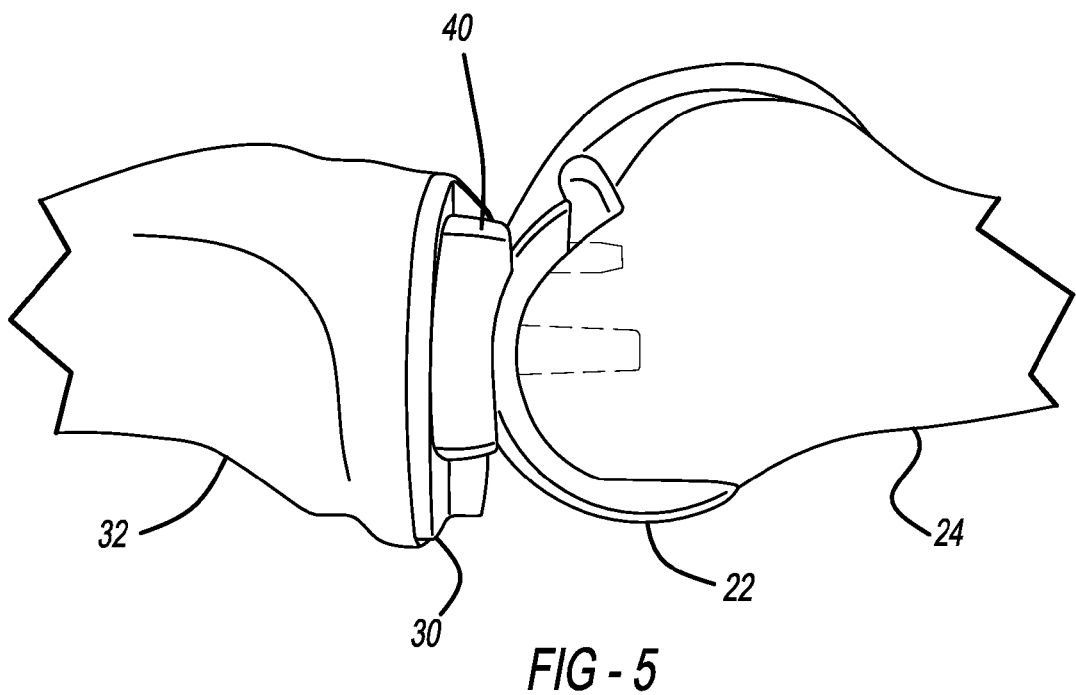
FIG. 5 is an environmental view of a femur, tibia, and prosthesis between the femur and tibia in extension.

With reference to FIG. 4, the bearing member 40 can move posteriorly when the femur 24 is in flexion relative to the tibia 32. Additionally, with reference to FIG. 5, the bearing member 40 can move anteriorly when the femur 24 is generally an extension relative to the tibia 32. Therefore, the bearing member 40 is generally selected to provide an appropriate tension between the femur 24 and the tibia 32 of the soft tissue that is maintained between the femur 24 and the tibia 32. Thus, the bearing member 40 may generally be positioned in a substantially or tight volume between the femur 24 and tibia 32. The bearing member 40 may also generally be selected to provide an appropriate or selected tension of the soft tissues and/or prosthetic replacements that interconnect the femur 24 and the tibia 32 following the implantation of the prosthetic system 20. The tensions of the soft tissue may provide a small and tight work area for insertion of the bearing member 40. Accordingly, an instrument, as discussed herein, may assist in placement of the bearing member 40.

Figure 6:
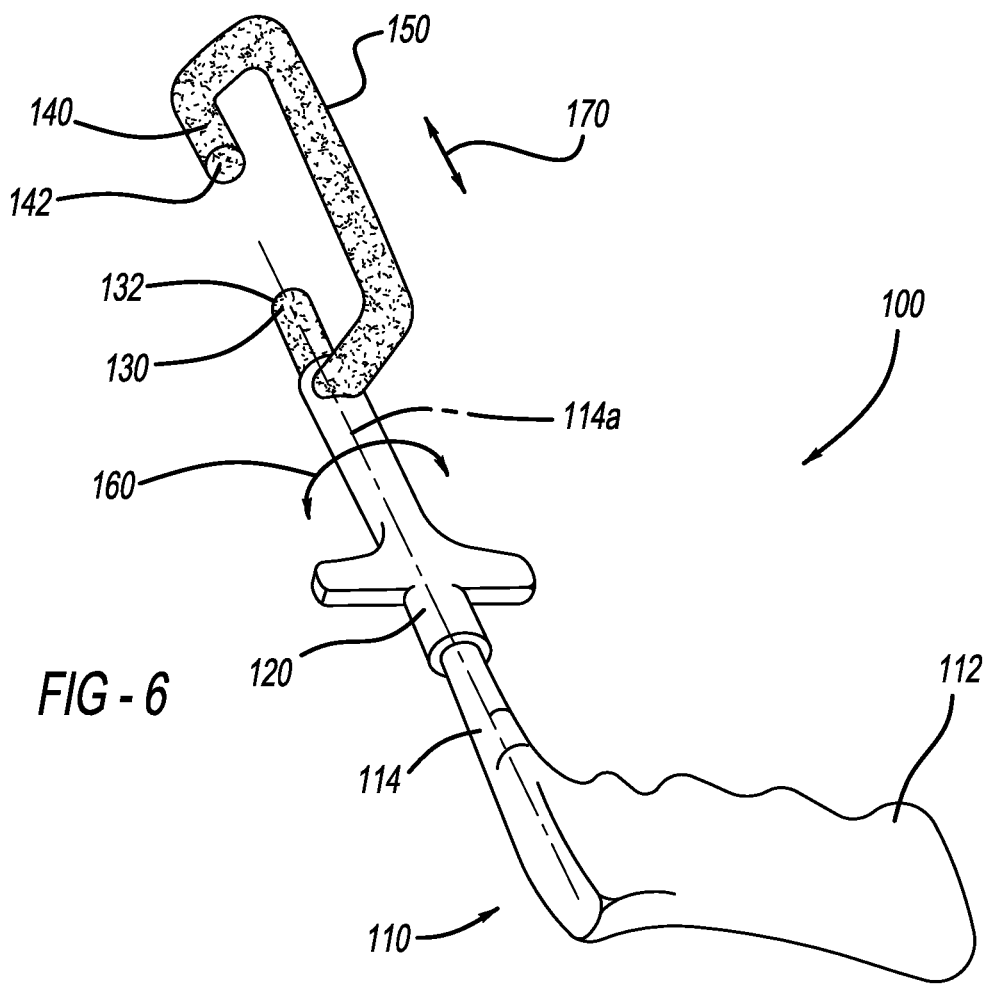
FIG. 6 is a perspective view of a bearing manipulation instrument according to various embodiments.

According to various embodiments, therefore, with reference to FIG. 6, a bearing insertion system or instrument 100 is illustrated. The bearing insertion system 100 can engage a bearing member 40a (FIG. 7) for positioning between the femoral component 22 and the tibial component 30. It is understood that the bearing member 40a may be a trial bearing member for trialing tension and range of motion or a prosthetic bearing member for implantation during use of the prosthetic system 20. It is further understood that the bearing member 40a may be both a trial bearing member and a prosthetic implant bearing member. Thus, a separate member for trialing and implantation for use of the prosthetic system 20 need not be provided.

The bearing insertion instrument 100 can generally include a graspable portion or handle 110. The graspable portion 110 can include a handle or a first member or first section 112 that is positioned at an angle relative to a second member or second section 114. The orientation of the first section 112 relative to the second section 114 can provide for a substantially ergonomic grasping of the instrument 100. For example, the configuration of the first section 112 relative to the second section 114 can be substantially pistol or pistol grip shape.

The second section 114 can be interconnected with a coupling member 120. The coupling member 120 can couple with a distal or terminal end of the second section 114 and/or pass over a length of the second section 114 such that a first bearing engaging portion 130 extends beyond the coupling member 120. The coupling member 120 may define an internal thread that cooperates with an external thread of the second section 114. Thus, rotating the coupling member 120 may move the coupling member 120 relative to the second section 114. The first bearing engaging portion 130 can be a terminal end of the second section 114 or be provided as a portion that engages and/or extends from the coupling member 120 separate from the second section 114.

According to various embodiments, however, the first bearing engaging portion 130 can be provided separate and opposed from a second bearing engaging portion 140. The second bearing engaging portion 140 can be provided or formed with an extension and surrounding arm 150. The two bearing engaging portions 130 and 140, therefore, can be opposed to each other to engage the bearing member 40a, as discussed further herein. The extension arm 150 can be coupled to the coupling member 120 according to various mechanisms, such as welding, adhesion, or being formed as a single piece with the coupling member 120. Further, the first bearing engaging portion 130, the second bearing engaging portion 140, and/or the extension arm 150, or other selected portions may be covered, coated, or overmolded with a selected material to cushion or protect the bearing member 40a and/or the anatomy. Selected covering materials can include silicone, radel, nylon, or other materials that can reduce or eliminate scratching of the prosthesis 20.

The coupling member 120 can be rotated generally in the direction of Arrow 160. Rotating the coupling member 120 can rotate the extension arm 150 around an axis 114a of the second section 114. Accordingly, the extension arm 150 can be rotated to various orientations relative to the first section 112. Thus, the extension arm 150 can be rotated to provide clearance for positioning the bearing member 40a relative to the positioned femoral component 22 and tibial component 30, such as for clearing the resected tibial wall 50 and soft tissue portions relative to the knee. Also, the extension arm 150 can be rotated for use with either the right or left knee.

Additionally, rotating the coupling member 120 can move the coupling member 120 relative to a distal end 132 of the first bearing engaging portion 130, such as via the threads discussed above. Also, a slot and groove engagement can provide axial movement of the coupling member 120 during rotation of the coupling member 120. The movement of the coupling member 120 relative to the distal end 132 of the first coupling portion moves a distal end 142 of the second coupling portion relative to the distal end 132 of the first bearing engaging portion 130. In this manner, the bearing member 40a can be engaged and disengaged from the instrument 100 by moving the second bearing engaging portion 140 generally in the direction of Arrow 170 to engage and disengage the bearing member 40a.

Figure 7:
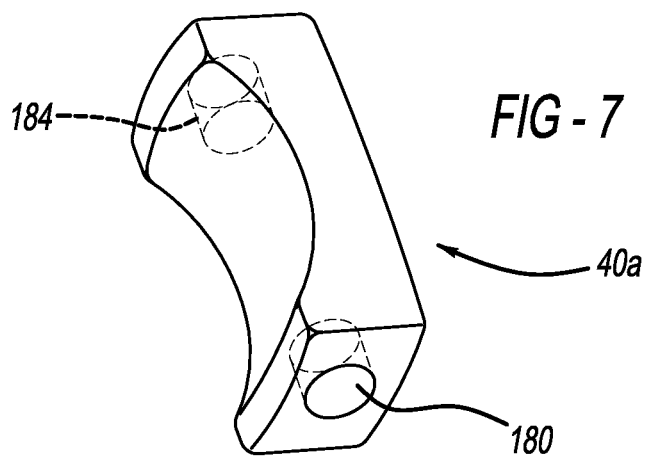
FIG. 7 is a perspective view of a bearing according to the present teachings.

The bearing member 40a can be engaged and disengaged with the instrument 100 relative to a first bore 180 and a second bore 184 in the bearing member 40a (FIG. 7). The first bore 180 can be engaged in the first bearing engaging portion 130 and a second bore 184 can be engaged with the second bearing engaging portion 140. The second bearing engaging portion 140 can be moved via the coupling member 120 to move the second bearing engaging portion 140 into the second bore 184. Further rotation of the coupling member 120 can urge the bearing member 40a to move the first bore 180 over the first bearing engaging portion 130. It is understood, however, that the bearing member 40a can be engaged between the first bearing engaging portion 130 and the second bearing engaging portion 140 by rotation of the coupling member 120 in an appropriately selected manner.

With reference to FIG. 8, an instrument 1000 can include the first section 112 and at least a portion of the second section 114, as discussed above. A coupling member 1120 can be provided to rotate relative to the second section 114 in a manner similar to that discussed above. Nevertheless, a first engaging portion 1130 can be formed as an elongated bar to extend from a first end 1131 and a second end 1132. A second engaging portion 1140 can include a second bar that extends from an end 1141 to a region 1142 that is coupled and extends from a coupling arm or extension arm 1150. Rotating the coupling member 1120 can move the second engaging portion 1140 generally in the direction of Arrow 1170 relative to the first engaging portion 1130. It is understood that the second engaging portion 1140 can move in either direction based upon rotation of the coupling member 1120. Rotation of the coupling member 1120 can move the first engaging portion 1130 relative to the second engaging portion 1140 to engage a bearing member 40a.

Bearing member 40b illustrated in FIGS. 9A and 9B can be a prosthetic implant bearing member or a trial bearing member, or a combination thereof. The bearing member 40b can include a first groove or depression 1200 and a second groove or depression 1210. The first groove or depression 1200 can be engaged by the first engaging portion 1130 and the second groove or depression 1210 can be engaged by the second engaging portion 1140. The bearing member 40b, once engaged, can be manipulated relative to the femoral component 22 and the tibial component 30. Again, the extension arm 1150 can be rotated relative to the graspable portion of the instrument 1000 to provide a clearance of various soft tissues and/or the bone portions, such as the tibial wall 50. Accordingly, the bearing member 40b can be positioned relative to the positioned femoral component 22 and tibial component 30 with the instrument 1000.

Figure 10:
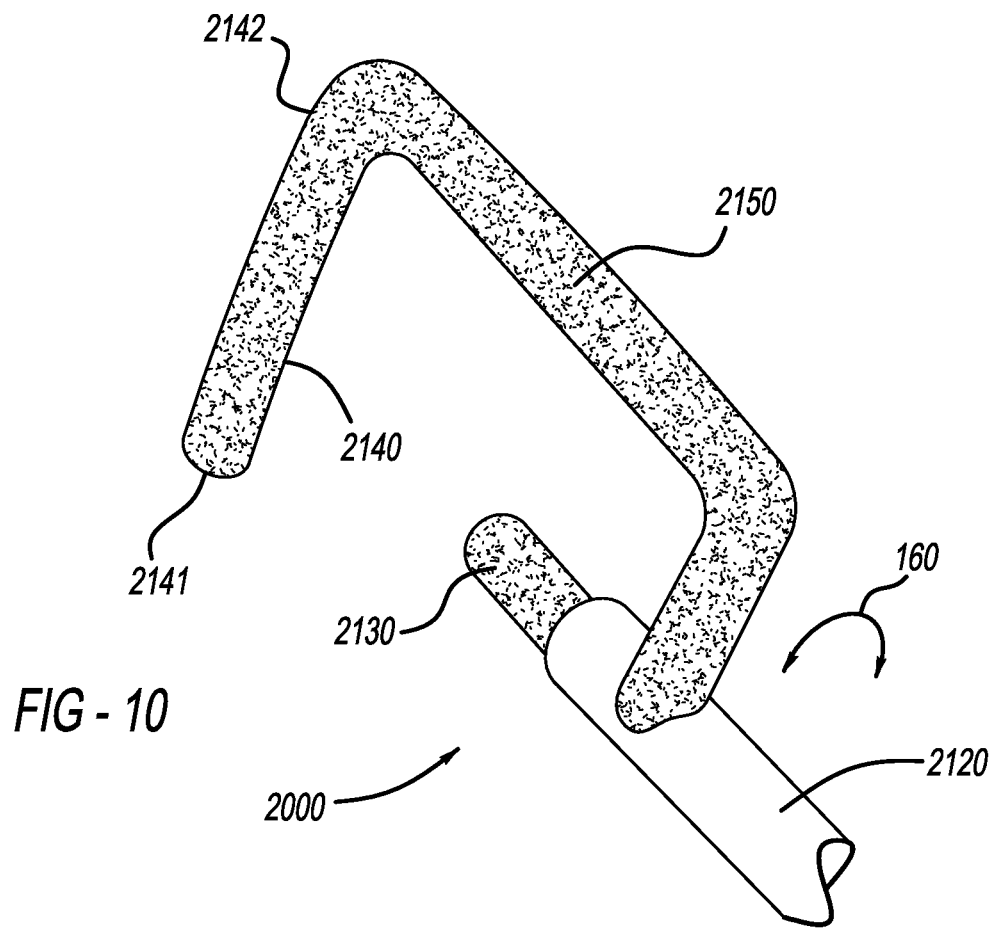
FIG. 10 is a perspective view of an additional bearing manipulation instrument according to the present teachings.
Figure 11:
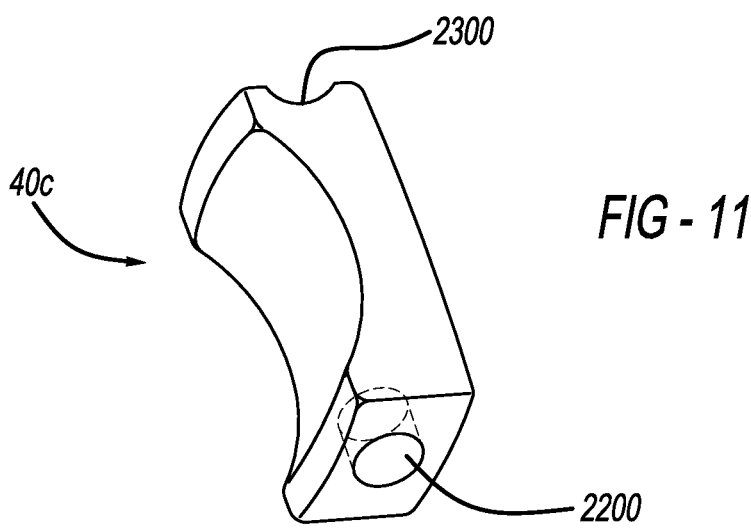
FIG. 11 is a perspective view of yet another bearing according to the present teachings.

With reference to FIG. 10, an instrument 2000 can include portions similar to the instrument 100, such as the first section 112 and at least a portion of the second section 114. The instrument 2000, however, can include a coupling portion 2120 that is positioned over the second section 114 and includes a detent, a first engaging portion, or a first coupling portion, member, or section 2130. Extending from the coupling member 2120 can be a second engaging portion or a second coupling portion 2140 that extends from an end 2141 to a section 2142. An extending arm 2150 can extend from the coupling member 2120 to the second engaging portion 2140. The coupling member 2120 can be rotated generally in the direction of Arrow 160, as discussed above, to move the first coupling section 2130 relative to the second coupling section 2140. Movement of the first coupling section 2130 relative to the second coupling section 2140 can allow for engagement and coupling to a bearing member 40c illustrated in FIG. 11.

The bearing member 40c can be a trial bearing member, an implantable prosthetic bearing member, or a trial and implantable bearing prosthetic. The bearing member 40c, however, can define or include a first bore 2200 to engage or receive the first engaging portion 2130. The bearing member 40c can further include a groove or a depression 2300 to engage or receive the second engaging portion 2140. Accordingly, the bearing member 40c can include a depression and a groove to receive respective projections and elongated members of the instrument 2000. Engagement of the bearing member 40c onto the instrument 2000 can provide for a substantially rigid connection to the first projection 2130 due to its receipt within the first bore 2200. The groove 2300 can then efficiently engage the second coupling portion 2140 without requiring precise placement of a second projection. Thus the instrument 2000 can allow for coupling to the bearing member 40c in a precise and rigid manner with speed and efficiency. During various operative procedures, it can be selected to perform the procedure with brevity for various purposes, such as reducing infection, time under anesthetic, and other patient concerns.

According to various embodiments, the first bearing engaging portions 130, 1130, 2130, the second bearing engaging portions 140, 1140, 2140, and/or the extension arms 150, 1150, 2150 or other selected portions may be covered, coated, or overmolded with a selected material to cushion or protect the bearing member 40a, 40b, 40c and/or the anatomy. Selected covering materials can include silicone, radel, nylon, or other materials that can reduce or eliminate scratching of the prosthesis 20. The instrument, according to various embodiments, however, may engage the bearing member in an appropriate manner.

Further, the bearing member, according to various embodiments, can be engaged in the instrument in various and selected manners. The bearing member, according to various embodiments, can be engaged within the instrument according to various engagement systems and techniques. For example, as discussed above, the second section 114 can extend through the coupling member 120, according to various embodiments, such that rotating the coupling member moves the second bearing engaging portion to engage and draw the bearing member towards the first engaging portion. In addition, or alternatively thereto, the coupling portion can be biased in either an open or a closed position, such as with a biasing spring. A user can overcome the biasing force on the coupling member to either engage or disengage the bearing member. For example, the coupling portion can be biased towards the first section 112 of the handle 110 into a closed position such that a user overcomes the biasing force to open the instrument to insert the bearing member and then the user allows the member to bias closed to engage the bearing member. The first engaging portion may also, or alternatively, be biased in either an open or a closed position. The bearing member can be inserted into the instrument against the biasing force of the first bearing engaging portion and the biasing force can then close the first bearing engaging portion to engage the bearing member. Additionally, or alternatively thereto, the first bearing engaging portion can be telescopically received or moveably received within the second section 114. A screw drive or threaded member, for example, can move the first bearing engaging section between an open and closed engaging position relative to the bearing member. Accordingly, it is understood that the bearing member can be engaged within the instrument, according to various embodiments, to hold the bearing member relative to the instrument, according to various embodiments, for inserting the bearing member relative to the other prosthetic portions.

Accordingly, it is understood that an instrument can be provided to engage a bearing member on at least two ends of the bearing member. The bearing member can include an end that is generally positioned near the anterior portion of the patient and an end that is positioned near a posterior portion of a patient. The instrument, according to various embodiments, as discussed herein, can engage the bearing member tightly and precisely for efficient positioning of the bearing member relative to the femoral component 22 and the tibial component 30. Additionally, the instrument, according to various embodiments can engage the bearing member by rotation of the coupling portion to tightly and securely engage the bearing member during a procedure. Nevertheless, rotation of a coupling member can also efficiently position portions of the instrument relative to the anatomy for reducing contact with portions of the anatomy and clearance for positioning the bearing member. Thus, the instrument can provide for efficient placement of the bearing for implantation and/or trialing of a prosthetic system.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to facilitate articulation of a femoral component and a tibial component, the system comprising:
   a bearing having a substantially planar distal surface configured to contact the tibial component, a proximal surface having a concave portion configured to receive the femoral component, a first end and a second end opposing the first end, the first end having a first instrument engaging feature and the second having a second instrument engaging feature;
   an instrument for engaging the bearing, the instrument comprising:
   a first bearing engaging portion configured to engage the first instrument engaging feature of the first end of the bearing;
   a second bearing portion configured to engage a second instrument engaging feature of the second end of the bearing; and
   a coupling member interconnecting the first and the second bearing engaging portions, the coupling member operable to move the second bearing engaging portion relative to the first bearing engaging portion to secure the bearing therebetween.

2. The system of claim 1, wherein the first bearing engaging portion includes a rod extending through the coupling member.

3. The system of claim 1, wherein the first bearing engaging portion is aligned with the second bearing engaging portion.

4. The system of claim 1, wherein the coupling member defines a through-bore from which the first bearing engaging portion extends, a first distal end of the first bearing engaging portion and a second distal end of the second bearing engaging portion are aligned along a longitudinal axis extending through an axial center of the through-bore.

5. The system of claim 1, wherein the coupling member includes an extension arm extending parallel to and laterally spaced apart from the first bearing engaging portion.

6. The system of claim 1, wherein the first and second bearing engaging portions include a covering selected from silicone or nylon.

7. The system of claim 1, wherein rotation of the coupling member moves the first and the second bearing engaging portions apart.

8. The system of claim 1, wherein the first bearing engaging portion extends in a first direction and the second bearing engaging portion extends in a second direction that is perpendicular to the first direction.

9. The system of claim 1, wherein the second bearing engaging portion includes a hook extending from the coupling member.

10. The system of claim 1, wherein the first and the second bearing engaging portions extend parallel to one another, and perpendicular to an extension arm coupling the second bearing engaging portion to the coupling member.

11. The system of claim 1, wherein the first instrument engaging feature comprises a first bore defined at the first end of the bearing, and the second instrument engaging feature comprises a second bore defined at the second end of the bearing.

12. The system of claim 1, wherein the first instrument engaging feature comprises a first groove defined at the first end of the bearing, and the second instrument engaging feature comprises a second groove defined at the second end of the bearing.

13. The system of claim 1, wherein the first instrument engaging feature comprises a bore defined at the first end of the bearing, and the second instrument engaging feature comprises a groove defined at the second end of the bearing.

14. The system of claim 1, wherein rotation of the coupling member in a first direction moves the first and the second bearing engaging portions apart, and wherein rotation of the coupling member in a second direction opposite to the first direction moves the first and the second bearing engaging portions together.

15. A system to facilitate articulation of a femoral component and a tibial component, the system comprising:
a bearing having a substantially planar distal surface configured to contact the tibial component, a proximal surface having a concave portion configured to receive the femoral component, an anterior end and a posterior end opposing the anterior end, the anterior end having a first instrument engaging the feature and the posterior end having a second instrument engaging feature;
an instrument for engaging the bearing, the instrument comprising:
a first bearing engaging portion configured to engage the first instrument engaging feature of the anterior end of the bearing;
a second bearing engaging portion configured to engage a second instrument engaging feature of the posterior end of the bearing; and
a coupling member including an extension arm interconnecting the first and the second bearing engaging portions, the coupling member defining a throughbore from which the first bearing engaging portion extends, the extension arm extending parallel to and spaced apart from a longitudinal axis extending through an axial center of the throughbore; wherein rotation of the coupling member moves the coupling member along the longitudinal axis to move the second bearing engaging portion relative to the first bearing engaging portion.

16. The system of claim 15, wherein the first bearing engaging portion extends in a first direction and the second bearing engaging portion extends in a second direction that is perpendicular to the first direction.

17. The system of claim 15, wherein a first distal end of the first bearing engaging portion is opposite to and faces a second distal end of the second bearing engaging portion.

18. The system of claim 15, wherein rotation of the coupling member in a first direction moves the first and the second bearing engaging portions apart, and wherein rotation of the coupling member in a second direction opposite to the first direction moves the first and the second bearing engaging portions together.

19. A system to facilitate articulation of a femoral component and a tibial component, the system comprising:
a bearing having a substantially planar distal surface configured to contact the tibial component, a proximal surface having a concave portion configured to receive the femoral component, a first end and a second end opposing the first end, the first end having a first female feature and the second end having a second female feature;
an instrument for engaging the bearing, the instrument comprising:
a first male feature configured to engage the first female feature of the first end of the bearing;
a second male feature configured to engage the second female feature of the second end of the bearing; and
an adjustment mechanism include a hook shaped extension arm interconnecting the second male feature with a body of the adjustment mechanism, the body configured to be moveable relative to the first male feature to move the second male feature relative to the first male feature to secure the bearing therebetween.

20. The system of claim 19, wherein the first male feature is aligned with the second male feature.

* * * * *

UNITED STATES PATENT AND TRADEMARK OFFICE
CERTIFICATE OF CORRECTION

PATENT NO. : 9,510,956 B2  
APPLICATION NO. : 14/196537  
DATED : December 6, 2016  
INVENTOR(S) : Duke A. Fox Page 1 of 1

It is certified that error appears in the above-identified patent and that said Letters Patent is hereby corrected as shown below:

On the Title Page

On page 2, in Column 2, under "Other Publications", Line 7, delete "Orhopedics," and insert --Orthopedics,--, therefor In the Claims In Column 8, Line 23, in Claim 1, after "second", insert --end--, therefor In Column 8, Line 30, in Claim 1, delete "a" and insert --the--, therefor (Second Occurrence)

In Column 8, Line 33, in Claim 1, after "and", delete "the", therefor

In Column 9, Line 30, in Claim 15, after "engaging", delete "the", therefor

In Column 9, Line 37, in Claim 15, delete "a" and insert --the--, therefor (Second Occurrence)

Signed and Sealed this  
Sixth Day of November, 2018

Andrei Iancu  
*Director of the United States Patent and Trademark Office*